United States Patent [19]
Bucher et al.

[11] Patent Number: 5,350,972
[45] Date of Patent: Sep. 27, 1994

[54] UV ABSORBING LAMP GLASS

[75] Inventors: Gerald L. Bucher, Canonsburg, Pa.; Christopher H. Welker, Lyndhurst, Ohio; Edward E. Hammer, Mayfield Village, Ohio; Curtis E. Scott, Mentor, Ohio; Thomas F. Soules, Richmond Heights, Ohio

[73] Assignee: General Electric Company, Schenectady, N.Y.

[21] Appl. No.: 66,642

[22] Filed: May 25, 1993

[51] Int. Cl.$^5$ .................. H01J 5/02; C03C 3/095; C03C 3/087; C03C 4/08
[52] U.S. Cl. ..................... 313/636; 313/493; 501/64; 501/70; 501/905
[58] Field of Search ............ 501/64, 70, 905; 313/493, 636

[56] References Cited

U.S. PATENT DOCUMENTS

| | | | |
|---|---|---|---|
| 2,860,059 | 11/1958 | Molter et al. | 501/70 X |
| 2,862,131 | 11/1958 | Escher-Desrivieres | 313/636 X |
| 4,015,966 | 4/1977 | Weaver | 501/70 X |
| 4,354,139 | 10/1982 | Konijnendijk et al. | 313/493 X |
| 4,677,481 | 6/1987 | Thomas et al. | 501/60 |
| 4,737,475 | 4/1988 | Thomas et al. | 501/60 |
| 4,792,536 | 12/1988 | Pecoraro et al. | 501/70 |
| 4,859,637 | 8/1989 | Roberts | 501/79 |
| 5,073,524 | 12/1991 | Speit | 501/60 |
| 5,077,133 | 12/1991 | Cheny et al. | 501/70 X |
| 5,112,778 | 5/1992 | Cheny et al. | 501/31 |
| 5,240,886 | 8/1993 | Gulotta et al. | 501/70 |

FOREIGN PATENT DOCUMENTS 0969689 10/1982 U.S.S.R. .................. 501/64

Primary Examiner—Mark L. Bell
Assistant Examiner—David R. Sample
Attorney, Agent, or Firm—Stanley C. Corwin; George E. Hawranko

[57] ABSTRACT

A UV absorbing soda-lime glass containing specific amounts of cerium oxide and iron oxide permits the use of significantly less $CeO_2$ than is used in prior art glass. The amount of cerium oxide and iron oxide present is 0.02–0.07 wt. % and 0.02–0.06 wt. %, respectively, with a combined total typically no more than 0.13 wt. %. This glass is useful for fluorescent lamp envelopes in absorbing UVB radiation having a wavelength between 280–320 nm, while being transparent to visible light radiation without effecting the color of the light emitted by the lamp.

6 Claims, 3 Drawing Sheets

UV ABSORBING LAMP GLASS

BACKGROUND OF THE INVENTION

1. Field of the Invention

This invention relates to UV absorbing glass useful for lamp envelopes. More particularly, this invention relates to a soda-lime glass which absorbs UV radiation below 320 nm and which contains both iron oxide and cerium oxide as the UV absorbing materials in the glass.

2. Background of the Disclosure

Electric arc discharge lamps having mercury in the arc discharge emit ultraviolet (hereinafter "UV") radiation which at wavelengths below 320 nm are harmful to the human eye, fabrics, plastics and other materials. Such lamps include fluorescent lamps, mercury vapor lamps and metal halide lamps. For high intensity arc discharge lamps such as the mercury vapor and metal halide lamps, UV emission has been substantially reduced or eliminated by the use of such lamps in fixtures having lenses which absorb UV radiation and also by using outer glass jackets surrounding the lamp wherein the jacket contains UV absorbing materials. With fluorescent lamps, the combination of one or more phosphor layers adjacent the inner wall of the lamp envelope and a lamp envelope containing relatively large amounts of iron oxide in the glass has been sufficient to reduce the UV radiation emitted by these lamps to satisfactory levels that are not harmful to the surrounding environment or to humans. Iron oxide absorbs UV radiation, including the harmful UVB radiation between 280-320 nm. However, the use of significant quantities of iron in lamp glass tends to make the glass slightly discolored, thereby reducing the visible light emitted by the lamp and effecting the color of the light.

UV absorbing glass for various uses such as lenses, insulators and lamp glass envelopes are known and have had incorporated therein various amounts of UV absorbing material such as oxides of titanium, cerium, iron, vanadium, manganese and the like. Many of these materials result in a green or brown tinted glass as is disclosed in U.S. Pat. No. 2,582,453. Combinations of cerium oxide along with vanadium oxide and titanium dioxide have also been disclosed in U.S. Pat. No. 2,862,131 and U.S. Pat. No. 3,148,300 as useful for UV absorbing soda lime glasses used for fluorescent lamp envelopes. However, the use of vanadium as an ingredient in glass presents its own problems in that vanadium oxide produces a glass with a greenish yellow or amber color, which glass has been suggested for tinted ophthalmic lenses (U.S. Pat. No. 2,582,453). Vanadium is also known to volatilize, thereby contaminating the surrounding atmosphere during the glass manufacturing process and it also combines with the surface of hot fire brick to form a low melting slag, thereby corroding the fire brick and reducing furnace life. Although cerium absorbs UV radiation, it is a comparatively expensive material and its use can significantly increase lamp cost, particularly when used in the quantities disclosed in the prior art. Consequently there is still a need for yet further improvements to UV absorbing soda-lime glass useful for lamp envelopes which will transmit the visible light emitted by the light source (the visible light region of the electromagnetic spectrum is about 400-720 nm) and at the same time eliminate or substantially reduce the UVB radiation emitted by the arc discharge having a wavelength between 280-320 nm. It would be particularly advantageous if the use of such a glass composition would not significantly increase the cost of manufacturing the lamp.

SUMMARY OF THE INVENTION

It has now been discovered that the inclusion of specific amounts of iron oxide and cerium oxide in soda-lime glass enables a reduction in the amount of cerium oxide used while still significantly reducing the UVB radiation emitted by the light source without imparting a color to the glass and thereby altering the color of the light emitted by the lamp. Thus, the present invention relates to a soda-lime glass containing both cerium oxide and iron oxide wherein the combined amount of said oxides ranges between 0.07-0.13 wt. % and preferably between 0.08-0.12 wt. % of the glass composition and to the use of such glass for a lamp envelope. The amount of cerium oxide will range between 0.02-0.1 wt. % and preferably 0.02-0.07 wt. % of the glass composition. The amount of iron oxide will range between 0.02-0.06 wt. % of the glass composition.

The UV absorbing glass of this invention has been found to be particularly useful as a lamp envelope for fluorescent lamps. Thus, in another embodiment the invention relates to a fluorescent lamp comprising a glass envelope enclosing an arc discharge light source within, at least one layer of phosphor material disposed adjacent the interior surface of said lamp envelope and wherein said lamp envelope comprises a soda-lime glass containing both cerium oxide and iron oxide wherein each of said oxides is present in said glass in the amounts set forth above.

DETAILED DESCRIPTION

Figure 1:
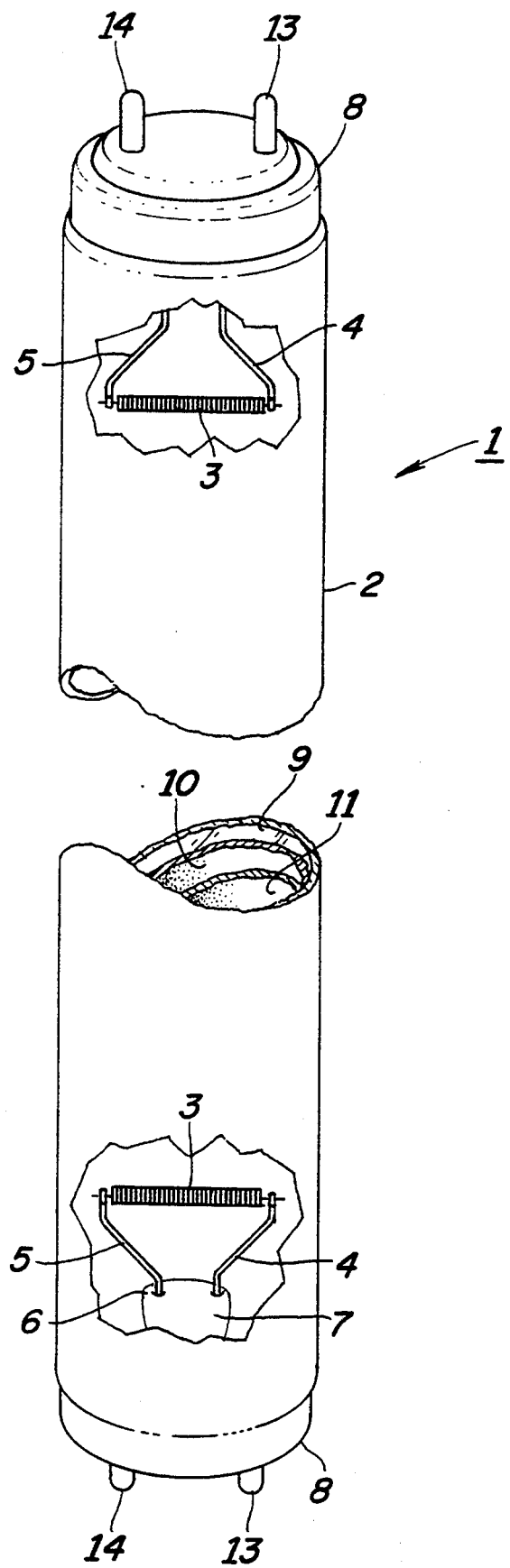
FIG. 1 schematically illustrates a fluorescent lamp having a soda-lime lamp glass envelope containing cerium oxide and iron oxide according to the invention.
Figure 2A:
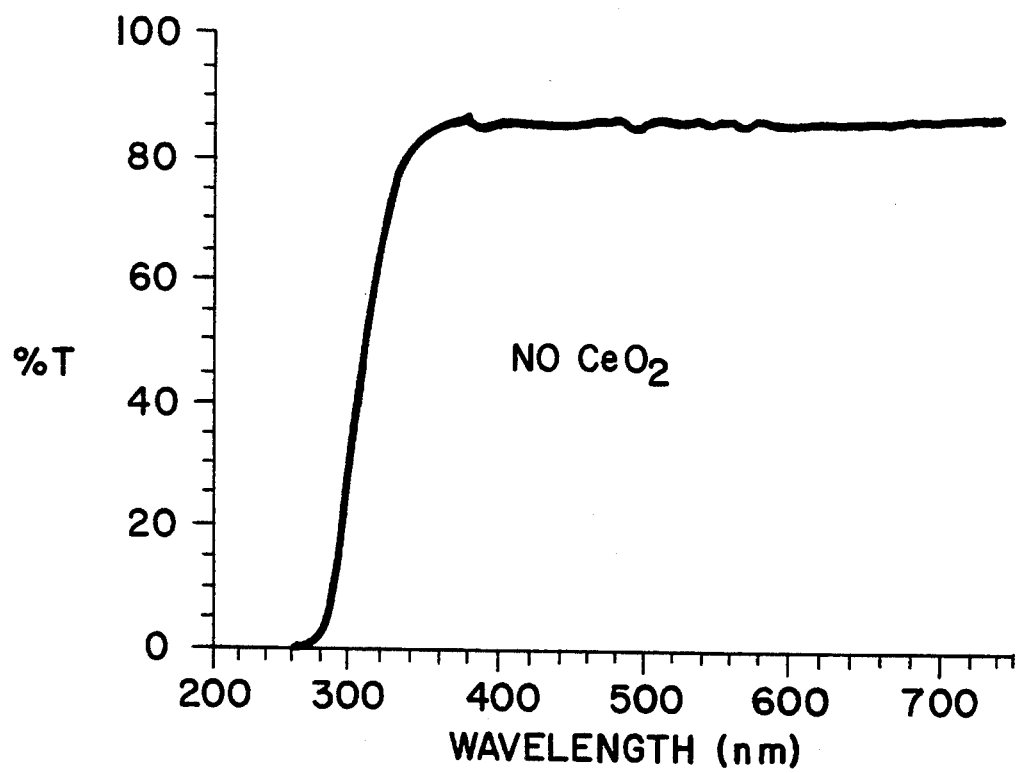
FIGS. 2(a) through 2(d) graphically illustrate percent transmission of a function of wavelength for soda-lime glass containing a fixed amount of iron oxide and different amounts of cerium oxide.
Figure 2B:
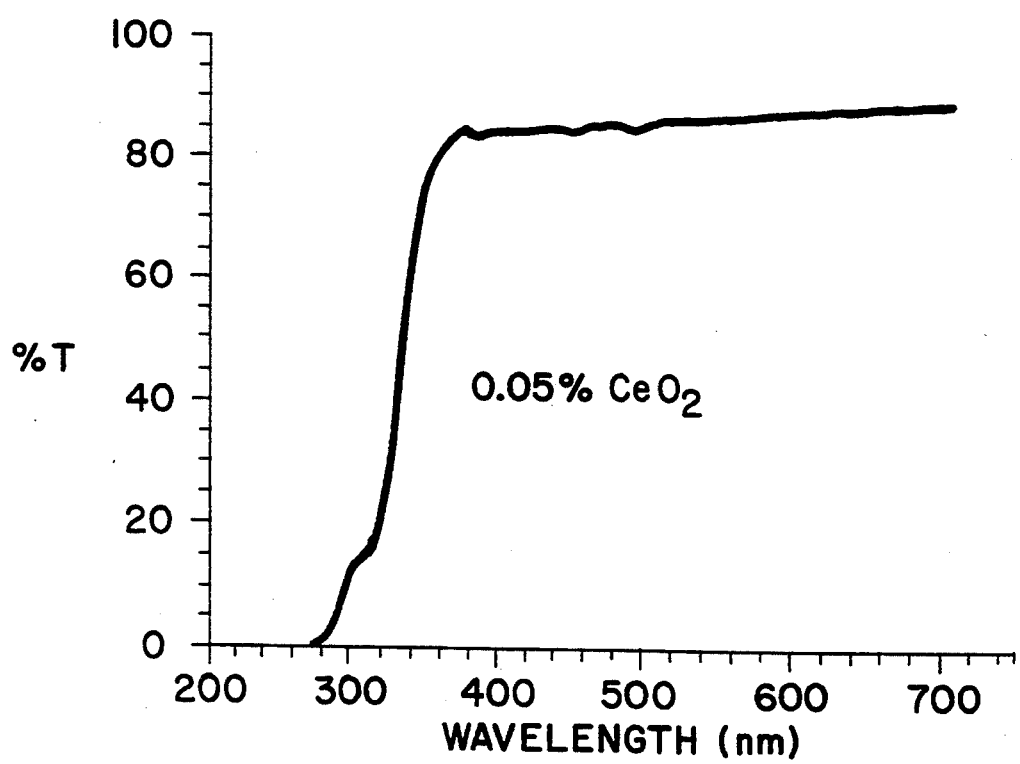
Figure 2C:
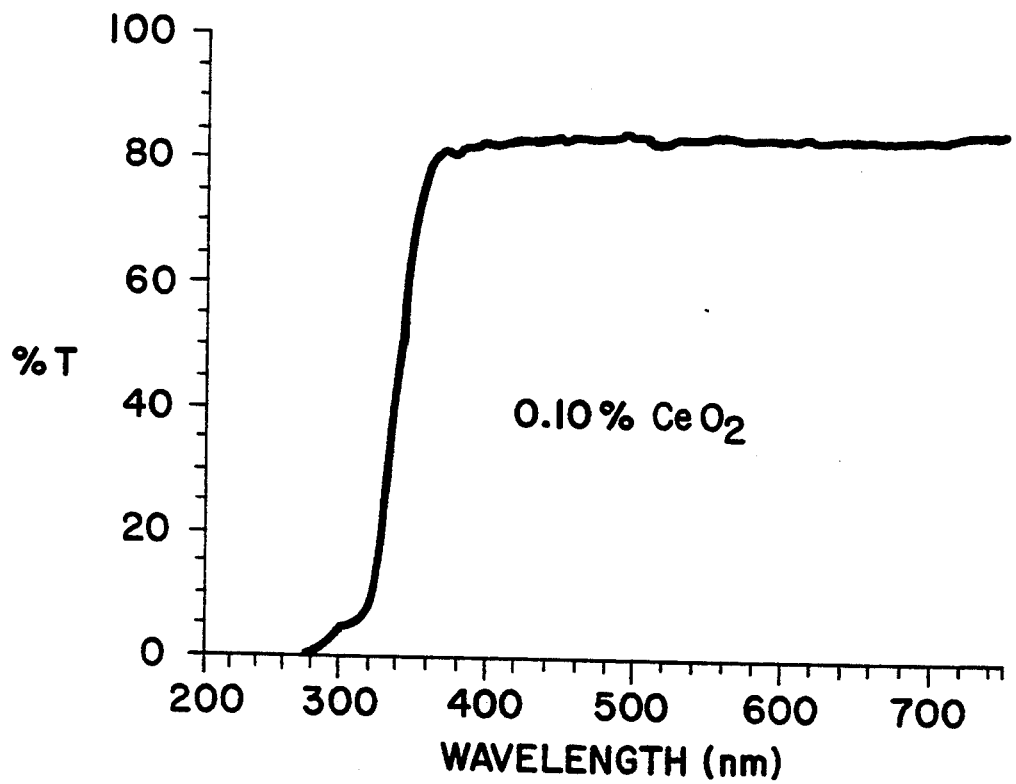
Figure 2D:
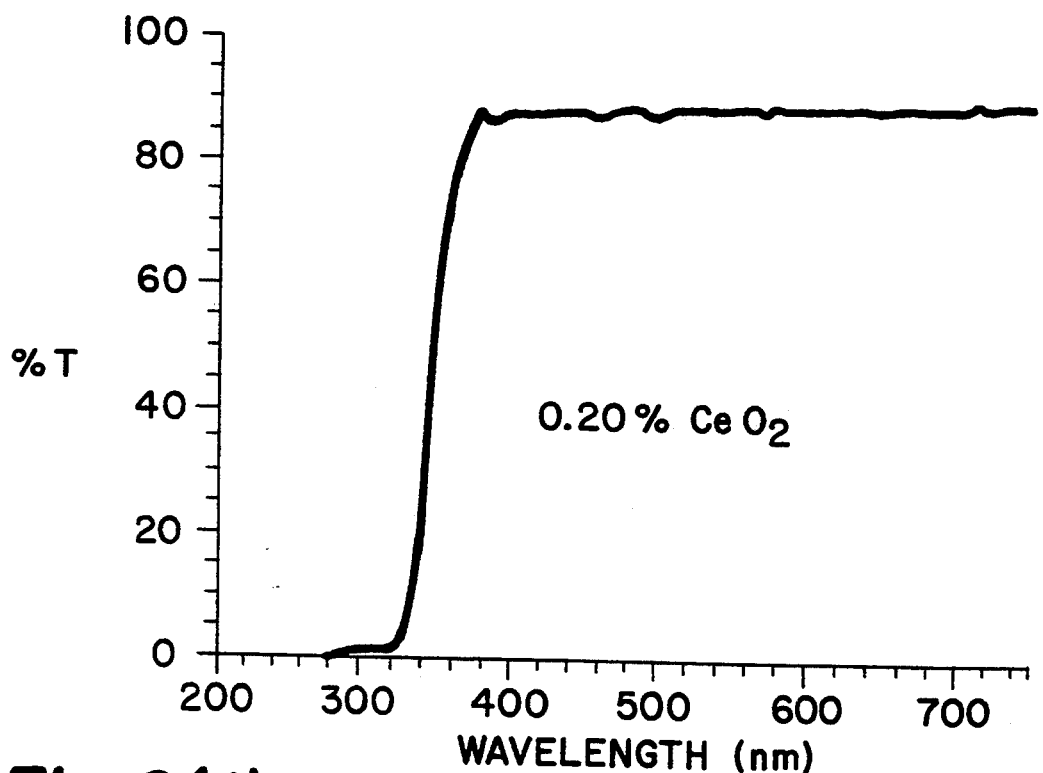

Referring to FIG. 1, fluorescent lamp 1 comprises an elongated, hermetically sealed glass envelope 2 made of a soda-lime glass according to the invention. Lamp 1 has electrodes 3 hermetically sealed within glass envelope 2. Envelope 2 contains a discharge-sustaining fill of mercury, along with an inert, ionizable gas (not shown). Electrodes 3 are connected to inlead wires 4 and 5 which extend through a glass seal 6 in a mount stem 7 to the electrical contacts of a base 8 fixed at both ends of the sealed glass envelope and containing electrical contact pins 13 and 14 which are electrically connected to inleads 4 and 5. The inert gas is a noble gas and will generally be argon or a mixture of argon and krypton under low pressure of about 1-4 torr. The inert gas acts as a buffer or means for limiting the arc current. Disposed on the inner wall 9 of envelope 2 is a light-transparent, conductive layer 10 typically consisting of tin oxide doped with minor amounts of antimony or fluorine to make it electrically conducting, since tin oxide of itself is a semiconducting material. The use of an electrically conducting tin oxide film and methods for applying it is known to those skilled in the art. However, in many fluorescent lamps a layer of tin oxide is not present and the invention is not limited to a fluorescent lamp having a tin oxide layer. Finally, a layer of phosphor 11 is disposed on tin oxide layer 10. One layer of phosphor, such as a calcium halophosphate phosphor, may be used or multiple layers of different phosphors and blends of different phosphors may be used as is well known to those skilled in the art. In operation, an electrical arc discharge is struck between electrodes 3 which ionizes the mercury causing it to give off UV; radiation. The UV radiation emitted by the arc discharge is converted by the phosphor layer 11 to visible light radiation which then passes out through glass envelope 9. The use of a UV absorbing glass according to the invention for glass envelope 9 absorbs substantially all of the UVB radiation emitted by the arc discharge which may pass through the phosphor layer 11 and out through glass envelope 9.

In yet another embodiment the UV absorbing glass of the invention may be employed as an outer jacket for other light sources which emit UV radiation, such as a mercury vapor arc discharge lamp or a metal halide arc discharge lamp, to absorb UV radiation emitted by these light sources. The use of glass outer jackets for such lamps is well known to those skilled in the art.

Those skilled in the art know that soda-lime glass in general may have a relatively wide range of compositions with which the invention may be practiced. A typical composition used in the manufacture of most fluorescent lamp envelopes may be the following in percentages by weight as calculated from the batch.

| Constituent | Percent |
| --- | --- |
| $SiO_2$ | 65–75% |
| $Na_2O$ | 12–20% |
| CaO | 4–6% |
| MgO | 3–4% |
| $Al_2O_3$ | 0.3–2.0% |
| $K_2O$ | 0.3–2.0% |
| $Fe_2O_3$ | 0.02–0.06% |

Small amounts of refining agents, such as antimony trioxide and/or sulfur trioxide may also be present, as well as small amounts of other materials, such as $TiO_2$, which are introduced into the batch from the raw materials as "can't help it" impurities. Typically, such a soda-lime glass has a strong UV absorption edge starting at around 360 nm as exhibited by about 5% of the UV radiation passing through a 0.03 inch glass plate being absorbed at a wavelength of 340 nm; 50% at 307 nm and >95% at wavelengths less than 287 nm. Hence, some, but not all of the UVB radiation from 280 nm–320 nm penetrates through this glass. The iron oxide, in this case ferric oxide ($Fe_2O_3$), content of the glass is generally determined by the amount of iron in the constituents used to make up the glass batch.

A suitable batch for a soda-lime glass falling within the oxide compositions above is the following in parts by weight:

| | |
| --- | --- |
| Sand | 1900 |
| Sodium carbonate | 750 |
| Dolomite | 420 |
| Nepheline syenite | 170 |
| Sodium nitrate | 22 |
| Sodium sulphate | 14 |
| Antimony trioxide | 7 |

The batch is melted at a temperature typically ranging between 1350° C.–1450° C. although higher and lower temperatures can be used as is known to those skilled in the art. Further, the batch is melted under an oxidizing environment (e.g., air). A soda-lime glass formed by the above batch had the following analyzed composition in percent by weight:

| Constituent | Percent |
| --- | --- |
| $SiO_2$ | 72.5 |
| $Na_2O$ | 17.1 |
| CaO | 4.9 |
| MgO | 3.2 |
| $Al_2O_3$ | 1.6 |
| $K_2O$ | 0.3 |
| $SO_3$ | 0.2 |
| $Sb_2O_3$ | 0.034 |
| $TiO_2$ | 0.026 |

The $SO_3$ and $Sb_2O_3$ are refining agents and the $TiO_2$ was present as an impurity in one of the batch ingredients. In the glass of the invention, the presence or absence of the $TiO_2$ does not effect the UV absorbing properties of the glass.

Four separate batches of soda-lime glass were made having the composition set forth above which contained 0.034 wt. % $Fe_2O_3$. The first batch had no $CeO_2$. The second, third and fourth batches had $CeO_2$ in an amount of 0.05 wt. %; 0.10 wt. % and 0.20 wt. %, respectively. Also, although the cerium is presented as $CeO_2$ based on the batch composition, the valence of the cerium in the glass may have been closer to 3+ than 4+. FIGS. 2(a) through 2(d) illustrate the percent transmission as a function of wavelength of each of these four batches of glass using flats at a thickness of 30 mils or 0.03 inches. One immediately sees that with an iron oxide content of 0.034%, but without the presence of the $CeO_2$, significant amount of UVB having a wavelength generally between 280 nm–320 nm is transmitted through the glass. In contrast, 0.05 wt. % $CeO_2$ in the glass along with 0.034% iron oxide absorbs a substantial amount (e.g., about 75%) of the UVB. Increasing the amount of $CeO_2$ up to 0.10% results in substantially all of the UVB between 280–320 nm absorbed by the glass. Further increasing the amount of cerium oxide to 0.20% does not result in a further significant increase in UVB absorption. It should be noted that the iron oxide and cerium oxide complement each other in absorbing the UVB radiation. Consequently, the amount of $CeO_2$ added to a glass batch will depend upon an analysis of the iron oxide or iron oxide precursor in the starting batch, inasmuch as greater amounts of iron oxide will require smaller amounts of cerium oxide and still achieve the same effective amount of UVB radiation absorption. Thus, the total combined amount of $CeO_2$ and $Fe_2O_3$ will typically be no more than 0.12% and more typically no greater than about 0.1%. For example, by means of an illustrative, but non-limiting example, the above glass compositions all had $Fe_2O_3$ present in an amount of 0.034 wt. % and it has been demonstrated that 0.05 wt. % of $CeO_2$ is sufficient to achieve a satisfactory amount of UVB absorption with this much iron oxide. If the glass batch had an amount of $Fe_2O_3$ of 0.06 wt. %, then substantially less $CeO_2$ would be required (e.g. 0.03 wt. %). Pure $CeO_2$ presently costs about $4.00 per pound which is about one hundred times more expensive for the glass batch composition without the $CeO_2$. Thus, one can readily appreciate the significance of the invention in reducing the amount of cerium oxide needed for UV absorption.

It is understood that various other modifications will be apparent to and can be readily made by those skilled in the art without departing from the scope and spirit of the invention. Accordingly, it is not intended that the scope of the claims appended hereto be limited to the description set forth above, but rather that the claims be construed as encompassing all of the features of patentable novelty which reside in the present invention, including all features which would be treated as equivalents thereof by those skilled in the art to which the invention pertains.

What is claimed is:

1. An electric arc discharge lamp having an arc discharge light source which emits both visible light radiation and UV radiation enclosed within a soda-lime glass envelope having a transmission of not more than about 25% of said UV radiation, wherein at least a portion of said UV radiation emitted has a wavelength between 280-320 nm, said soda-lime glass comprising cerium oxide, predominantly in the form of $CeO_2$, present in an amount of from 0.02 to 0.1 wt. % of said glass composition and iron oxide, predominantly in the form of $Fe_2O_3$, present in an amount of from 0.02 to 0.06 wt. % of said glass composition.

2. A lamp according to claim 1 wherein the combined amount of said cerium oxide and iron oxide present in said glass ranges between 0.07-0.13 wt. % of said glass composition.

3. A fluorescant lamp having a mercury arc discharge light source which emits UV radiation between 280-320 nm enclosed within a soda-lime glass envelope, wherein said glass comprises the following oxide composition in weight percent:

| | |
|---|---|
| $SiO_2$ | 65-75% |
| $Na_2O$ | 12-20% |
| CaO | 4-6% |
| MgO | 3-4% |
| $Al_2O_3$ | 0.3-2.0% |
| $K_2O$ | 0.3-2.0% |
| $CeO_2$ | .02-.1% |
| $Fe_2O_3$ | .02-.06% |

4. A lamp according to claim 2 wherein said cerium oxide is present in an amount of 0.02-0.07 wt. % of the glass.

5. A glass according to claim 3 wherein the combined amount of said cerium oxide and said iron oxide in said glass is 0.07-0.13 wt. %.

6. A glass according to claim 4 wherein said combined amount of said cerium oxide and said iron oxide present in said glass is 0.08-0.12 wt. %.

* * * * *